United States Patent
Minai et al.

[11] 3,970,694
[45] July 20, 1976

[54] CYCLOALKYL PHENOXY CARBOXYLIC ACID DERIVATIVES

[75] Inventors: Masayoshi Minai, Moriyama; Yoshio Suzuki, Itami; Noritaka Hamma, Sakai; Eiichi Murayama, Takarazuka; Shunji Aono, Toyonaka, all of Japan

[73] Assignee: Sumitomo Chemical Company, Limited, Osaka, Japan

[22] Filed: June 28, 1974

[21] Appl. No.: 484,063

[30] Foreign Application Priority Data
July 2, 1973   Japan.................. 48-75031

[52] U.S. Cl.................. 260/520 C; 260/473 G; 260/473 S; 424/308; 424/317
[51] Int. Cl.²................................ C07C 63/33
[58] Field of Search............ 260/520, 473 G, 520 C

[56] References Cited
UNITED STATES PATENTS

| | | | |
|---|---|---|---|
| 2,370,256 | 2/1945 | Niederl.................. | 260/520 |
| 3,470,235 | 9/1969 | Jackson et al.............. | 260/520 |
| 3,716,583 | 2/1973 | Nakamura et al............. | 260/520 |

*Primary Examiner*—Norman Morgenstern
*Attorney, Agent, or Firm*—Stevens, Davis, Miller & Mosher

[57] ABSTRACT
Novel compounds having the formula,

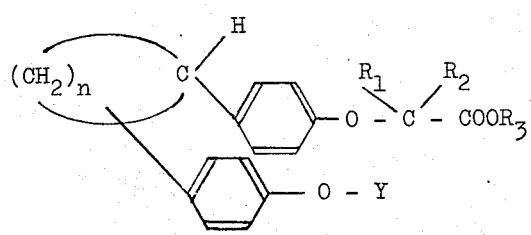

wherein $R_1$, $R_2$ and $R_3$ are each independently hydrogen or a $C_1$–$C_4$ alkyl; $n$ is an integer of 4–6; and Y is hydrogen or a group of the formula

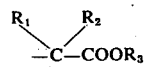

wherein $R_1$, $R_2$ and $R_3$ are as defined above.

These compounds are produced, for example, by reacting a bisphenolic compound of the formula,

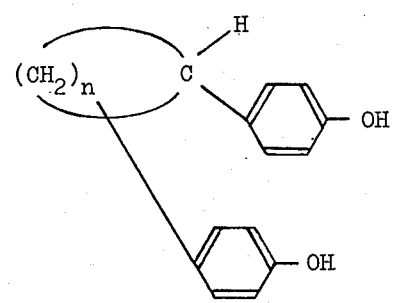

with chloroform and a ketone compound of the formula,

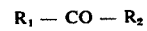

$$R_1 - CO - R_2$$

in the presence of an alkali. Alternatively, they are produced by reacting the bisphenolic compound with α-halogeno- or α-hydroxycarboxylic acid derivative of the formula,

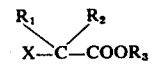

wherein $R_1$, $R_2$, and $R_3$ are as defined above, and X is a halogen or hydroxyl. The novel compounds are anti-atherosclerosis agents useful for lowering elevated levels of cholesterol or lipids.

5 Claims, No Drawings

CYCLOALKYL PHENOXY CARBOXYLIC ACID DERIVATIVES

This invention relates to novel anti-atherosclerosis agents. More particularly, the invention pertains to novel agents which are useful for the lowering of elevated levels of cholesterol or lipids.

Atherosclerosis is an adult disease for which there is no known satisfactory cure. Although the cause for atherosclerosis is not yet known in spite of discussions in the academic circles, it has broadly been recognized that one of the most significant histophthological manifestations of atherosclerosis is the deposition of lipids in the blood. Accordingly, research has been directed to the disturbed metabolism of lipids, and attention has been given to the extraordinarily elevated level of cholesterol in the blood.

A number of experimental and clinical facts have been reported, which indicate the relationship between atherosclerosis and elevated blood cholesterol or lipid level. Hence, the development of agents to reduce the elevated blood cholesterol or lipid level is considered extremely important for the prevention of atherosclerosis.

Concentrated efforts have heretofore been made for the development of such agents for lowering cholesterol or lipids and a number of compounds have been tested clinically, but none of them have been proved to be completely satisfactory. Some of them are fairly effective but produce significantly harmful side effects, and others have inadequate effectiveness, so that they are required to be administered in large doses.

A group of compounds practically employed presently for the above purpose includes ethyl α-(p-chlorophenoxy)isobutyrate. However, its effectiveness is not very high, and it has a tendency to produce harmful side effects such as hypertrophy of the liver.

The present inventors have found a group of novel compounds which are effective as cholesterol-lowering agents and which are substantially nontoxic.

It is therefore an object of the present invention to provide cholesterol- or lipid-lowering agents.

Another object is to provide a process for preparing cholesterol- or lipid-lowering agents.

A further object is to provide pharmoceutical compositions containing such agents.

Other objects will be apparent from the following description.

In order to accomplish the above objects the present invention provides novel cycloalkyl phenoxy carboxylic acid derivatives of the formula,

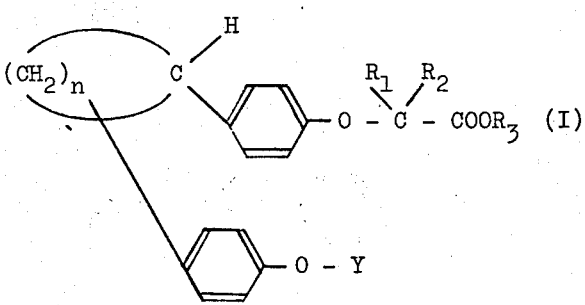

wherein $R_1$, $R_2$ and $R_3$ are hydrogen or a $C_1$–$C_4$ alkyl; $n$ is an integer of 4–6; and Y is hydrogen or a group of the formula,

wherein $R_1$, $R_2$, and $R_3$ are as defined above.

Examples of $R_3$ include methyl, ethyl, n-propyl, isopropyl, n-butyl, iso-butyl and t-butyl.

These cycloalkyl phenoxy carboxylic acid derivatives (I) may be prepared by any of the procedures as shown by the following reaction scheme:

Procedure 1

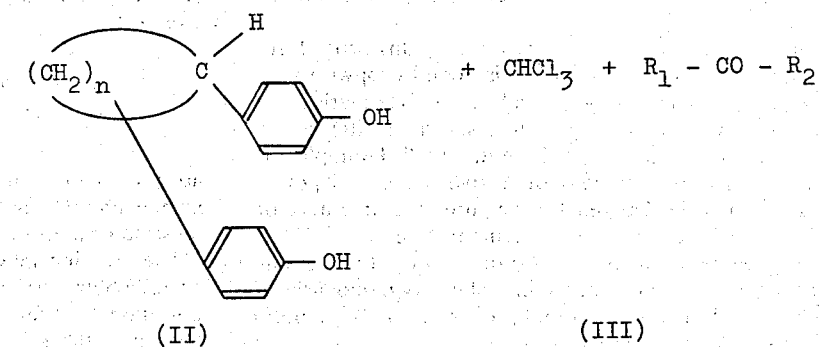

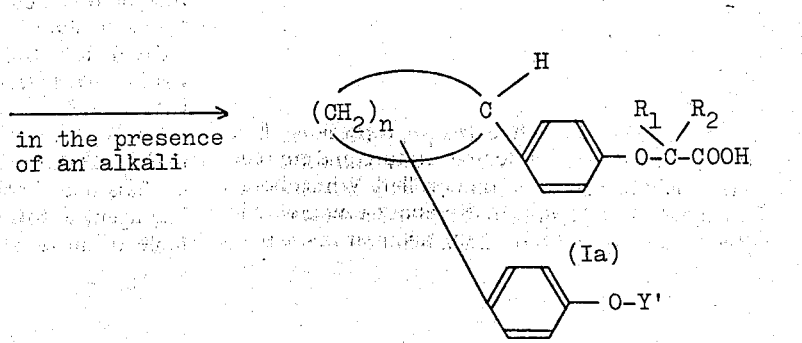

Procedure 2

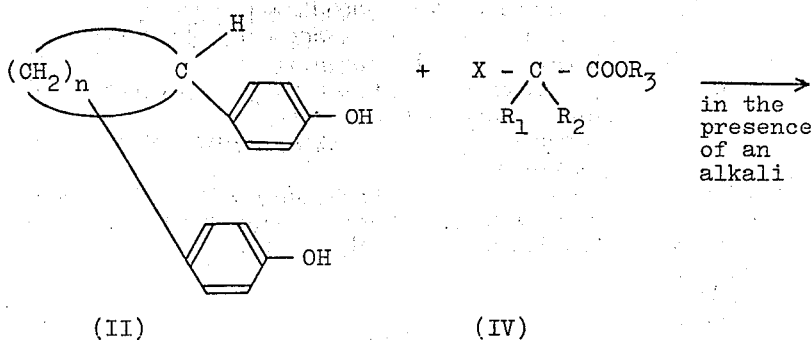

(II)                    (IV)

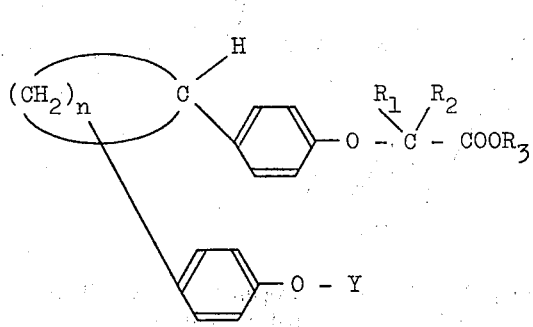

wherein X is halogen or hydroxyl, $R_1$, $R_2$, $R_3$, $n$ and Y are as defined above; and Y' is hydrogen or a group of the formula,

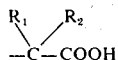

wherein $R_1$ and $R_2$ are as defined above.

The above procedures are illustrated in detail as follows:

Procedure 1

Reaction of a bisphenol derivative (II) with chloroform and a keto-compound (III) in the presence of an alkali In order to carry out the reaction of this procedure, at least 1 mole of chloroform is added dropwise to a mixture containing 1 mole of a bisphenol derivative (II) and at least 1 mole of a keto-compound (III) in the presence of at least 3 moles of an alkali. Examples of the alkali used include sodium hydroxide and potassium hydroxide. The reaction requires a temperature of 0°–150°C, and ordinarily a temperature of 5°–70°C, and a reaction time of 3–40 hours. In order to obtain as the main product one of either a phenoxy monocarboxylic acid derivative (Ia) (i.e., Y' = H) or a phenoxy dicarboxylic acid derivative (Ia)

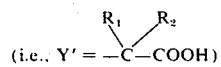

the reaction conditions such as the proportions of the reactants used, the reaction temperature and the reaction time should be carefully controlled. When about 1 mole of the keto-compound (III), about 1 mole of chloroform and about 3 moles of the alkali are used per 1 mole of the bisphenol derivative (II), a phenoxy monocarboxylic acid derivative (Ia) (i.e., Y' = H) is obtained as the main product. On the other hand, when the keto-compound, chloroform and the alkali are used in excessive amount, a bisphenoxy dicarboxylic acid derivative (Ia)

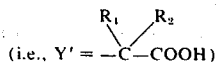

is obtained as the main product.

When a phenoxy monocarboxylic acid derivative (Ia) (i.e., Y' = H) and a phenoxy dicarboxylic acid derivative (Ia)

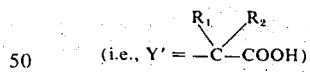

are produced at the same time, they can be separated from each other by a usual purification method such as recrystallization or chromatography.

The reaction may be carried out in the presence of excess chloroform and the keto-compound (III) in the presence or absence of an inert reaction medium. Examples of the reaction medium include dioxane, benzene, toluene, etc.

Procedure 2

Condensation reaction of a bisphenol derivative (II) with an α-halogeno- or hydroxy-carboxylic acid derivative (IV)

When X is a halogen, 1 mole of a bisphenol derivative (II) is dissolved or suspended in an inert reaction medium and contacted with at least 1 mole of an alkaline agent to form an alkaline salt, and then at least 1 mole of an α-halogenated carboxylic acid derivative (IV) (i.e., X = halogen) is added to the resultant reaction mixture to effect the condensation reaction. When the reaction is completed, the reaction mixture is further subjected to usual purification procedure to give the desired phenoxy carboxylic acid derivative (I). Examples of the inert reaction medium used in this process include benzene, toluene, methanol, ethanol, ether, dioxane, dimethylsulfoxide, N,N-dimethylformamide, etc. Examples of the alkaline agent used include potassium hydroxide, sodium hydroxide, alkali metal alcoholates, alkali metal carbonates, methallic sodium, sodium hydride and organic tertiary amines such as trimethylamine, triethylamine and pyridine. The reaction requires a temperature of 0°–120°C.

In order to obtain, as the chief product, either a phenoxy monocarboxylic acid derivative (I) (i.e., Y = H) or a phenoxy dicarboxylic acid derivative

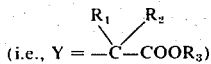

(i.e., $Y = -\overset{R_1}{\underset{R_2}{C}}-COOR_3$)

the reaction conditions such as the proportions of the reactants, the reaction temperature and the reaction time should be carefully controlled. If the alkaline agent and/or the α-halogeno carboxylic acid derivative (IV) are used in an amount equimolar with the bisphenol derivative (II), a phenoxy monocarboxylic acid derivative (I) (i.e., Y = H) is mainly obtained. On the other hand, if two or more mols of both the alkaline agent and the α-halogeno carboxylic acid derivative (IV) are used per mole of the bisphenol derivative (II), a phenoxy dicarboxylic acid derivative (I)

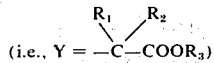

(i.e., $Y = -\overset{R_1}{\underset{R_2}{C}}-COOR_3$)

is mainly obtained.

When X is hydroxyl, 1 mole of a bisphenol derivative (II) is contacted with at least 1 mole of an α-hydroxy carboxylic acid derivative (IV) (i.e., X = OH) in the presence of an acidic catalyst such as sulfuric acid, p-toluenesulfonyl chloride, aresenic acid, boric acid, sodium hydrogen sulfate, potassium hydrogen sulfate, etc. in the presence or absence of an inert reaction medium. Examples of the reaction medium used include benzene, toluene, dioxane, etc. The acid catalyst is used in an amount of 0.01–0.5 mole per 1 mole of a bisphenol derivative. The reaction requires a temperature of 10°–90°C.

In order to obtain, as the chief product, either a phenoxy monocarboxylic acid derivative (I) (i.e., Y = H) or a phenoxy dicarboxylic acid derivative (I)

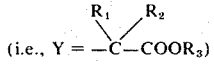

(i.e., $Y = -\overset{R_1}{\underset{R_2}{C}}-COOR_3$)

as described above, the reaction conditions such as the proportions of the reactants, the reaction temperature and the reaction time should be carefully controlled.

A phenoxy carboxylic acid derivative (Ia) or its reactive ester is converted into an ester by usual esterification procedures, for example, by treatment with an esterifying agent. In this process, the term "reactive ester" of the phenoxy carboxylic acid derivative (Ia) means an acyl halide, an acid anhydride, an ester of the acid, a salt of the acid, etc, and the term "esterification agent" means an alcohol, diazomethane, a dialkyl sulfate, an alkyl halide, an alkyl halogenosulfite, etc.

In the present invention, the phenoxy carboxylic acid derivative (I) wherein $R_3$ is hydrogen and/or Y is hydrogen can be converted to a salt by treatment with an alkali. The salt is formed at the carboxyl and/or phenolic hydroxyl. An alkali metal salt can be obtained by contacting the phenoxy carboxylic acid derivative (I) wherein $R_3$ is hydrogen and/or Y is hydrogen with sodium hydroxide, potassium hydroxide, sodium carbonate, potassium carbonate, sodium bicarbonate or ammonia, etc., or with an alcoholate of an alkali metal such as sodium methylate in an organic solvent, preferably in a lower alkanol such as methanol or ethanol, or with hydroxide, carbonate or bicarbonate of an alkali metal in an organic solvent, preferably in acetone or methanol, if necessary in the presence of a small amount of water. The alkali metal salt thus obtained can be converted to an alkaline earth metal salt by treatment with a salt of an alkaline earth metal such as calcium chloride.

Bisphenol derivatives of the formula (II) employed as a starting material are exemplified by 1,2-bis(4'-hydroxyphenyl)-cyclohexane, 1,3-bis(4'-hydroxyphenyl)cyclohexane, 1,4-bis(4'-hydroxyphenyl)-cyclohexane, 1,2-bis(4'-hydroxyphenyl)cyclopentane, 1,3-bis(4'-hydroxyphenyl)cyclopentane, 1,2-bis(4'-hydroxyphenyl)cycloheptane, 1,3-bis(4'-hydroxyphenyl)-cycloheptane and 1,4-bis(4'-hydroxyphenyl)-cycloheptane. And, for example, 1,2-bis(4'-hydroxyphenyl)cyclohexane can be obtained by a method disclosed in J. Amer. Chem. Soc., 71, 3313 (1949), 1,3-bis(4'-hydroxyphenyl)cyclohexane by a method disclosed in J. Amer. Chem. Soc., 73, 2377 (1951), and 1,4-bis(4'-hydroxyphenyl)cyclohexane by a method disclosed in J. Amer. Chem. Soc., 74, 5631 (1952).

According to the present invention, the following cycloalkyl phenoxy carboxylic acid derivatives are obtained.

Cyclo $C_5H_8$-1,2-(p-$C_6H_4$O$CH_2CO_2H)_2$
Cyclo $C_5H_8$-1,2-(p-$C_6H_4$OCH($CH_3$)$CO_2H)_2$
Cyclo $C_5H_8$-1,2-(p-$C_6H_4$OC($CH_3)_2CO_2H)_2$
Cyclo $C_5H_8$-1,2-(p-$C_6H_4$OC($CH_3$)($C_2H_5$)$CO_2H)_2$
Cyclo $C_5H_8$-1,2-(p-$C_6H_4$OC($CH_3$)(n-Propyl)$CO_2H)_2$
Cyclo $C_5H_8$-1,2-(p-$C_6H_4$OC($C_2H_5)_2CO_2H)_2$ and 1,3-isomers
Cyclo $C_6H_{10}$-1,2-(p-$C_6H_4$O$CH_2CO_2H)_2$
Cyclo $C_6H_{10}$-1,2-(p-$C_6H_4$OCH($CH_3$)$CO_2H)_2$
Cyclo $C_6H_{10}$-1,2-(p-$C_6H_4$OC($CH_3)_2CO_2H)_2$
Cyclo $C_6H_{10}$-1,2-(p-$C_6H_4$OC($CH_3$)($C_2H_5$)$CO_2H)_2$
Cyclo $C_6H_{10}$-1,2-(p-$C_6H_4$OC($CH_3$)(n-propyl)$CO_2H)_2$
Cyclo $C_6H_{10}$-1,2-(p-$C_6H_4$OC($C_2H_5)_2CO_2H)_2$ and 1,3-, 1,4-isomers
Cyclo $C_7H_{12}$-1,2-(p-$C_6H_4$O$CH_2CO_2H)_2$
Cyclo $C_7H_{12}$-1,2-(p-$C_6H_4$OCH($CH_3$)$CO_2H)_2$
Cyclo $C_7H_{12}$-1,2-(p-$C_6H_4$OC($CH_3)_2CO_2H)_2$
Cyclo $C_7H_{12}$-1,2-(p-$C_6H_4$OC($CH_3$)($C_2H_5$)$CO_2H)_2$
Cyclo $C_7H_{12}$-1,2-(p-$C_6H_4$OC($CH_3$)(n-propyl)$CO_2H)_2$
Cyclo $C_7H_{12}$-1,2-(p-$C_6H_4$O($C_2H_5)_2CO_2H)_2$ and 1,3, 1,4-isomers
Cyclo $C_5H_8$-1,2-(B)-p-$C_6H_4$O$CH_2CO_2H$
Cyclo $C_5H_8$-1,2-(B)-p-$C_6H_4$OCH($CH_3$)$CO_2H$
Cyclo $C_5H_8$-1,2-(B)-p-$C_6H_4$OC($CH_3)_2CO_2H$
Cyclo $C_5H_8$-1,2-(B)-p-$C_6H_4$OC($CH_3$)($C_2H_5$)$CO_2H$
Cyclo $C_5H_8$-1,2-(B)-p-$C_6H_4$OC($CH_3$)(n-propyl)-$CO_2H$
Cyclo $C_5H_8$-1,2-(B) p-$C_6H_4$OC($C_2H_5$)$CO_2H$ and 1,3 isomers Cyclo $C_6H_{10}$-1,2-(B)-p-$C_6H_4OCH_2CO_2H$
Cyclo $C_6H_{10}$-1,2-(B)-p-$C_6H_4OCH(CH_3)CO_2H$
Cyclo $C_6H_{10}$-1,2-(B)-p-$C_6H_4OC(CH_3)_2CO_2H$
Cyclo $C_6H_{10}$-1,2-(B)-p-$C_6H_4OC(CH_3)(C_2H_5)CO_2H$
Cyclo $C_6H_{10}$-1,2-(B)-p-$C_6H_4OC(CH_3)(n\text{-propyl})CO_2H$
Cyclo $C_6H_{10}$-1,2-(B)-p-$C_6H_4OC(C_2H_5)_2CO_2H$ and 1,3, 1,4-isomers
Cyclo $C_7H_{12}$-1,2-(B)-p-$C_6H_4OCH_2CO_2H$
Cyclo $C_7H_{12}$-1,2-(B)-p-$C_6H_4OCH(CH_3)CO_2H$
Cyclo $C_7H_{12}$-1,2-(B)-p-$C_6H_4OC(CH_3)_2CO_2H$
Cyclo $C_7H_{12}$-1,2-(B)-p-$C_6H_4OC(CH_3)(C_2H_5)CO_2H$
Cyclo $C_7H_{12}$-1,2-(B)-p-$C_6H_4OC(CH_3)(n\text{-propyl})CO_2H$
Cyclo $C_7H_{12}$-1,2-(B)-p-$C_6H_4OC(C_2H_5)_2CO_2H$ and 1,3 1,4-isomers
Methyl esters of the above-mentioned acids
Ethyl esters of the above-mentioned acids
n-Propyl esters of the above-mentioned acids
iso-Propyl esters of the above-mentioned acids
n-Butyl esters of the above-mentioned acids
iso-Butyl esters of the above-mentioned acids
t-Butyl esters of the above-mentioned acids
Na salts of the above-mentioned acids
K salts of the above-mentioned acids
Ca salts of the above-mentioned acids
Mg salts of the above-mentioned acids
$NH_4$ salts of the above-mentioned acids
Al salts of the above-mentioned acids In the above exemplified compounds, "B" means a group of the formula

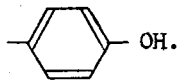

The present invention further provides a pharmaceutical composition containing a cycloalkyl phenoxy carboxylic acid derivative of the formula,

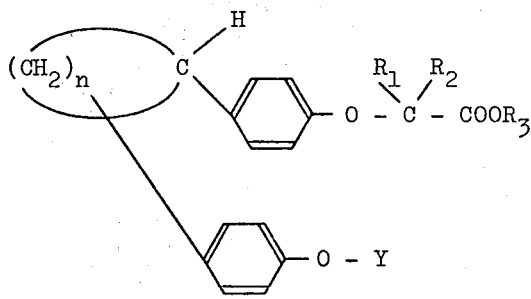

wherein $R_1$, $R_2$ and $R_3$ are each independently hydrogen or a $C_1 - C_4$ alkyl; $n$ is an integer of 4 to 6; and Y is hydrogen or a group of the formula,

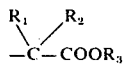

wherein $R_1$, $R_2$ and $R_3$ are as defined above, and at least one pharmaceutically acceptable carrier.

The cholesterol-lowering agents of the invention may, for example, be orally administered. Usually the amount orally administered is 0.01–10 g. per day/human adult, and preferably 0.05 –3 g. per day/human adult. The cholesterol-lowering agents may be in any suitable conventional form for oral administration. Thus they may be encased in a capsule, or they may be in liquid form, tablet form, or in the form of a powder. In preparing the agents in these various forms, the active compound may be mixed with or impregnated in a pharmaceutically acceptable carrier such as lactose, potato starch, corn starch, cellulose derivatives, gelatin, corn oil, cotton seed oil, etc.

The cholesterol-lowering activity of the present compounds in mice was tested by injecting them intravenously with 500 mg/kg of Triton WR 1339 (Trademark for oxyethylated tert-octylphenol formaldehyde polymer manufactured by Rohm & Haas Co., U.S.A.).

The test compounds were orally administered in a dose of 12.5 mg/kg immediately after the injection. The mice were killed, and the analysis of serum cholesterol was carried out.

The cholesterol-lowering effect was calculated using the following equation:

$$\text{Cholesterol-lowering effect } (\%) = \frac{C - T}{C - N} \times 100$$

where $C$ = serum cholesterol level (mg/100 ml) in a group of 24 mice measured after injecting the mice with Triton and before treatment with a test compound.

$T$ = serum cholesterol level (mg/100 ml) in a group of 12 of the mice injected with Triton and also treated with a test compound, measured after injection and treatment, and N = serum cholesterol level (mg/100 ml) in a group of 12 untreated mice (i.e. no Triton or test compound administered).

An example of the results obtained in this test is shown in Table 1. In Table 1 compounds are referred to by number of the Examples.

Table 1

| Compounds (No.) | Cholesterol-lowering effect (%) |
| --- | --- |
| 1 | 31 |
| 2 | 33 |
| 3 | 34 |
| 4 | 58 |
| 5 | 32 |
| 6 | 65 |
| 7 | 58 |
| 8 | 17 |
| 9 | 15 |
| 10 | 15 |
| Clofibrate* | 17** |

*Trademark for ethyl-p-chlorophenoxyisobutyrate produced by I.C.I.
**Only clofibrate was tested by administering in a dose of 50 mg/kg.

The present invention will be illustrated in more detail with reference to the following examples, which are only illustrative, but not limitative.

Example 1

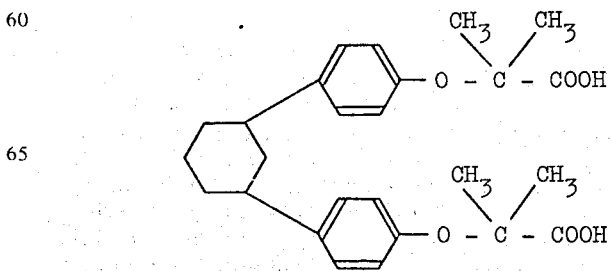

To a mixture of 15 g. of 1,3-bis(4'-hydroxyphenyl)-cyclohexane and 250 g of acetone was added 75 g. of potassium hydroxide. Then 40 g. of chloroform was added to the mixture with stirring at 10°–20°C., and the mixture was heated at 30°–40°C for 3 hours to complete the reaction. Thereafter the reaction mixture was concentrated to give a residue. After the residue was dissolved in water, the solution was treated with activated charcoal and acidified by dilute hydrochloric acid to give an oily substance. The oily substance was extracted with ether and the ether solution was extracted again with an aqueous dilute Na$_2$CO$_3$ solution. The separated alkaline aqueous layer was acidified and extracted with ether. The ether layer was dried over anhydrous sodium sulfate and concentrated to give a crude product, which was purified by recrystallization from toluene. The desirable phenoxy dicarboxylic acid was obtained, 18 g., m.p. 160.5°–162°C.

Elementary analysis: Calculated (%) C: 70.89; H: 7.32; Found (%) C: 70.78; H: 7.30.

EXAMPLES 2–6

According to a procedure similar to that disclosed in Example 1, the following compounds were obtained as shown in Table 2.

Table 2

| Example No. | Bisphenol | Starting material R$_1$COR$_2$ ketone g | KOH NaOH g | CHCl$_3$ g (temp.) | Reaction times (hours) temp. (°C) |
|---|---|---|---|---|---|
| 2 | 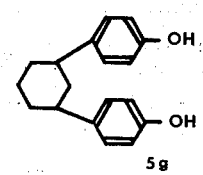 5g | CH$_3$COC$_2$H$_5$ 80 g | KOH 5 g | 3 g (10°–20°C) | 3 (30–40) |
| 3 | 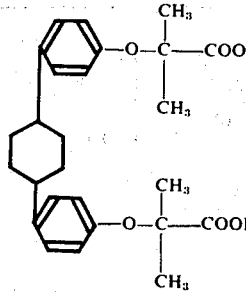 | CH$_3$COCH$_3$ 150 g | KOH 50 g | 27 g (10°–20°C) | 3 (30–40) |
| 4 | 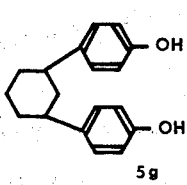 5g | CH$_3$COC$_2$H$_5$ 100 g | KOH 15 g | 8 g (15°–25°C) | 3 (15–25) 1 (40) |
| 5 | 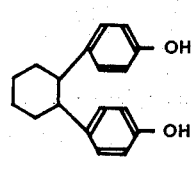 10g | CH$_3$COC$_2$H$_5$ 200 g | KOH 35 g | 20 g (15°–25°C) | 3 (15–25) 3 (30–40) |

Table 2-continued
| No. | Chemical structure | | | | | |
|---|---|---|---|---|---|---|
| 6 | 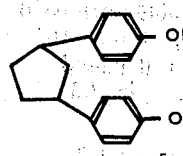 5g | CH₃COC₂H₅ 100 g | KOH 20 g | 15 g (15°–25°C) | 2 (5–25) 3 (30–40) | |
| 7 | 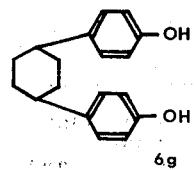 6g | CH₃COC₂H₅ 150 g | KOH 33 g | 17 g (15°–25°C) | 2 (15–25) 3 (30–40) | |
| Chemical structure | Product Physical property | Elementary analysis Calculated (%) | Found (%) |
|---|---|---|---|
| 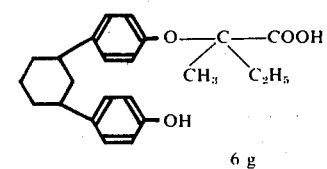 6 g | m.p. 147.5–149° C | C 74.97 H 7.66 | 74.84 7.58 |
| 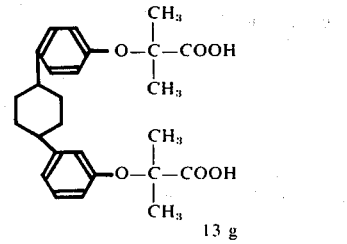 13 g | m.p. 138–140°C | C 70.89 H 7.32 | 70.84 7.33 |
| 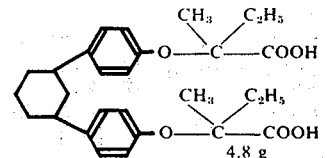 4.8 g | $n_D^{27.5}$ 1.5441 | C 71.77 H 7.74 | 71.81 7.68 |
| 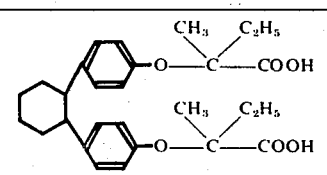 10.5 g | $n_D^{26}$ 1.5477 | C 71.77 H 7.74 | 71.59 7.82 |

Table 2-continued

| Structure | | Analysis | |
|---|---|---|---|
| (cyclopentane-bis-phenyl-O-C(CH₃)(C₂H₅)-COOH, 4.3 g) | $n_D^{25}$ 1.5435 | C 71.34<br>H 7.54 | 71.46<br>7.51 |
| (cyclohexane-bis-phenyl-O-C(CH₃)(C₂H₅)-COOH, 5.5 g) | $n_D^{23.5}$ 1.5344 | C 71.77<br>H 7.74 | 71.51<br>7.93 |

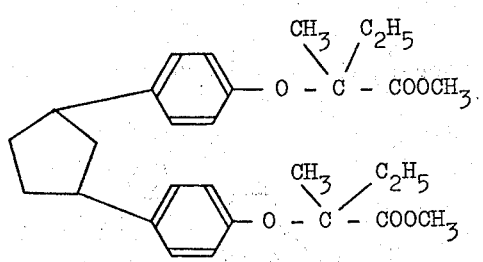

To a mixture of 3 g. of 1,3-bis(4'-hydroxyphenyl)cyclopentane and 25 ml. of dry toluene was added 0.5 g. of sodium methoxide. Then 3 g. of 2-bromo-2-methylbutyric acid methyl ester dissolved in toluene was gradually added dropwise to the mixture with stirring. The mixture was heated at 60°–80°C for 10 hours. The reaction mixture was then washed with water. Thereafter, toluene was distilled off, and the residue was purified in chromatography column packed with activated alumina. The desirable ester was obtained, 2.5 g., $n_D^{27}$ 1.5215

Elementary analysis: Calculated (%) C: 72.17; H: 7.94; Found (%) C: 72.24; H: 7.89.

EXAMPLES 9–10

According to a procedure similar to that disclosed in Example 8, the following compounds were obtained as shown in Table 3.

Table 3

| Example No. | Bisphenol | Starting material Br—C(R₁)(R₂)—COOR₃ | Base | Solvent ml. | Reaction time (hours) Temp. (°C) |
|---|---|---|---|---|---|
| 9 | (cyclohexane-bis-phenyl-OH, 5 g) | Br—C(CH₃)(C₂H₅)—COOCH₃, 7 g | NaH 0.5 g | Toluene 80 ml | 10 hours (80–100) |
| 10 | (cyclohexane-bis-phenyl-OH, 5 g) | Br—C(CH₃)(C₂H₅)—COOCH₃, 4 g | CH₃ONa 0.8 g | Toluene 30 ml | 10 hours (60–80) |

Table 3-continued

| Chemical structure | Product Physical property | Elementary analysis Calcd. (%) | Found (%) |
|---|---|---|---|
| (structure with two CH₃/C₂H₅-C-COOCH₃ groups on cyclohexane-linked phenyl rings) 7.2 g | $n_D^{25}$ 1.5243 | C 72.55 H 8.12 | 72.59 8.08 |
| (structure with two CH₃/C₂H₅-C-COOCH₃ groups on cyclohexane-linked phenyl rings) 4.3 g | $n_D^{25}$ 1.5225 | C 72.55 H 8.12 | 72.41 8.21 |

What is claimed is:

1. A compound of the formula,

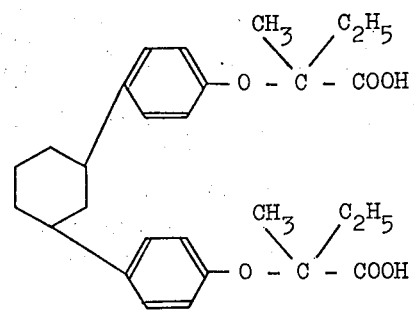

2. A compound of the formula,

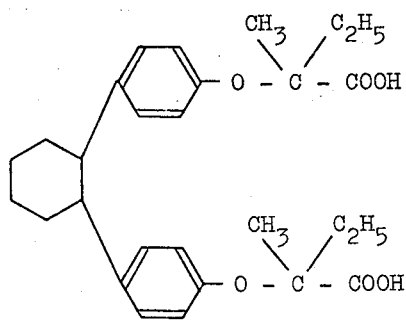

3. A compound of the formula,

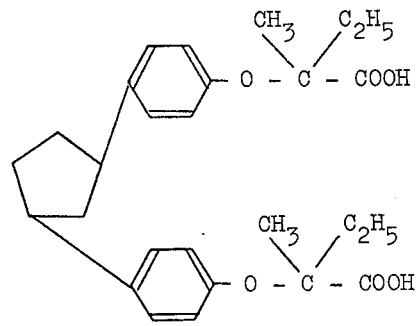

4. A compound of the formula,

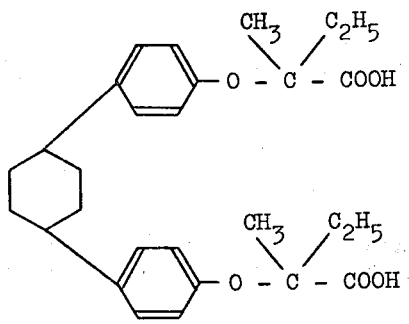

5. A compound of the formula,

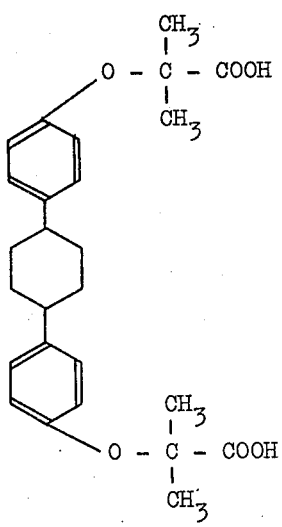

* * * * *